United States Patent [19]

Song

[11] Patent Number: 5,364,627
[45] Date of Patent: Nov. 15, 1994

[54] GRADUAL RELEASE STRUCTURES MADE FROM FIBER SPINNING TECHNIQUES

[75] Inventor: Joo H. Song, Northbrook, Ill.

[73] Assignee: Wm. Wrigley Jr. Company, Chicago, Ill.

[21] Appl. No.: 918,897

[22] Filed: Jul. 21, 1992

Related U.S. Application Data

[63] Continuation of Ser. No. 418,662, Oct. 10, 1989, abandoned.

[51] Int. Cl.$^5$ .............................................. A61F 13/00
[52] U.S. Cl. ................................... 424/443; 424/405; 424/484; 426/548; 71/64.13
[58] Field of Search .................. 424/443, 78, 405, 484

[56] References Cited

U.S. PATENT DOCUMENTS

| | | | |
|---|---|---|---|
| 2,224,430 | 12/1940 | Garbutt | 107/8 |
| 3,028,308 | 4/1962 | Zambito et al. | 167/82 |
| 3,201,353 | 8/1965 | Corben | 252/316 |
| 3,329,574 | 7/1967 | Barron et al. | 167/82 |
| 3,435,110 | 3/1969 | Nichols | 424/20 |
| 3,737,521 | 6/1973 | Born | 424/22 |
| 3,795,744 | 3/1974 | Ogawa et al. | 426/3 |
| 3,818,107 | 6/1974 | Yolles | 426/3 |
| 3,923,939 | 12/1975 | Baker et al. | 264/49 |
| 3,928,633 | 12/1975 | Shoat et al. | 426/96 |

(List continued on next page.)

FOREIGN PATENT DOCUMENTS

| | | | |
|---|---|---|---|
| 2005362 | 6/1990 | Canada | A23G 3/30 |
| 0040048 | 11/1981 | European Pat. Off. | D01F 9/04 |
| 0122808 | 10/1984 | European Pat. Off. | A23G 3/30 |
| 0126827 | 12/1984 | European Pat. Off. | A01N 25/20 |
| 0191986 | 8/1986 | European Pat. Off. | A23G 9/30 |
| 0252374 | 1/1988 | European Pat. Off. | A23P 1/04 |
| 0253554 | 1/1988 | European Pat. Off. | A61K 9/22 |
| 0263224 | 4/1988 | European Pat. Off. | A23G 3/30 |
| 0273009 | 6/1988 | European Pat. Off. | A23G 3/30 |
| 0288909 | 11/1988 | European Pat. Off. | A23G 3/30 |
| 0370296 | 5/1990 | European Pat. Off. | A23G 3/30 |
| 0376549 | 7/1990 | European Pat. Off. | A23G 3/30 |
| 0484124 | 5/1992 | European Pat. Off. | A23G 3/30 |
| 0492981 | 7/1992 | European Pat. Off. | A23G 3/30 |
| 2503989 | 10/1982 | France | A23G 3/30 |
| 2220103 | 4/1987 | France | A23L 1/236 |
| 61-296118 | 10/1986 | Japan . | |
| 62-215010 | 9/1987 | Japan . | |
| 63-175067 | 7/1988 | Japan . | |
| 63-295711 | 12/1988 | Japan . | |
| 1-124619 | 5/1989 | Japan . | |
| 1-174609 | 7/1989 | Japan . | |
| 1-183514 | 7/1989 | Japan . | |
| 1-246411 | 10/1989 | Japan . | |
| 1327761 | 8/1973 | United Kingdom | A23L 1/26 |
| WO85/03414 | 8/1985 | WIPO | A23L 1/22 |
| WO88/08298 | 11/1988 | WIPO | A61K 9/00 |
| WO89/02703 | 4/1989 | WIPO | A23G 3/30 |
| WO90/07859 | 7/1990 | WIPO | A23G 3/30 |
| WO90/07864 | 7/1990 | WIPO . | |
| WO90/08478 | 8/1990 | WIPO | A23L 1/187 |
| WO90/12511 | 11/1990 | WIPO | A23G 3/30 |
| WO91/07103 | 5/1991 | WIPO | A23G 3/30 |

OTHER PUBLICATIONS

F. Billmeyer, Jr., *Textbook of Polymer Science*, 518–22 (Wiley International Edition, 2nd).

R. Dunn, D. Lewis, L. Beck, *Fibrous Polymers for the Delivery of Contraceptive Steroids to the Female Reproductive Tract*, Controlled Release of Pesticides and Pharmaceuticals, 125–46 (D. Lewis Ed. 1981).

Primary Examiner—D. Gabrielle Phelan
Attorney, Agent, or Firm—Willian Brinks Hofer Gilson & Lione

[57] ABSTRACT

A delivery system and a process for making the system is provided for the gradual release of an active agent. The system comprises an active agent and a wall material. The delivery system is formed by melt spinning a mixture of particles of active agent and wall material into a fiber. The fiber has a longitudinal dimension and a cross sectional dimension, the cross sectional dimension being no greater than about 1 mm. The fiber has an exterior surface. The particles of active agent are dispersed throughout the wall material such that the particles of active agent are gradually released from the fiber when the fiber is contacted with a solvent specific to the active agent.

29 Claims, 6 Drawing Sheets

U.S. PATENT DOCUMENTS

| | | | |
|---|---|---|---|
| 3,951,821 | 4/1976 | Davidson | 252/1 |
| 4,122,195 | 10/1978 | Bahoshy et al. | 426/3 |
| 4,125,519 | 11/1978 | Goodman et al. | 528/363 |
| 4,139,639 | 12/1979 | Bahoshy et al. | 426/3 |
| 4,206,301 | 6/1980 | Yolles | 536/3 |
| 4,226,886 | 10/1980 | Lakes | 428/304 |
| 4,230,687 | 10/1980 | Sair et al. | 424/22 |
| 4,374,858 | 2/1983 | Glass et al. | 426/5 |
| 4,384,004 | 5/1983 | Cea et al. | 426/3 |
| 4,384,005 | 5/1983 | McSweeney | 426/250 |
| 4,386,106 | 5/1983 | Merritt et al. | 426/5 |
| 4,388,328 | 6/1983 | Glass | 426/3 |
| 4,399,154 | 8/1983 | Puglia et al. | 426/5 |
| 4,447,475 | 5/1984 | Lubbock et al. | 427/213.31 |
| 4,485,118 | 11/1984 | Carroll et al. | 426/5 |
| 4,490,395 | 12/1984 | Cherukuri et al. | 426/3 |
| 4,496,592 | 1/1985 | Kuwahara et al. | 426/5 |
| 4,515,769 | 5/1985 | Merritt et al. | 424/49 |
| 4,556,566 | 12/1985 | Bell | 426/96 |
| 4,556,567 | 12/1985 | Meyer | 426/96 |
| 4,568,560 | 2/1986 | Schobel | 427/3 |
| 4,590,075 | 5/1986 | Wei et al. | 426/5 |
| 4,606,940 | 8/1986 | Frank et al. | 427/213.32 |
| 4,643,593 | 1/1987 | Stroz et al. | 426/5 |
| 4,673,565 | 6/1987 | DiLuccio et al. | 424/443 |
| 4,673,577 | 6/1987 | Patel | 426/5 |
| 4,689,235 | 8/1987 | Barnes et al. | 426/89 |
| 4,690,825 | 9/1987 | Won | 424/501 |
| 4,695,463 | 9/1987 | Yang et al. | 424/440 |
| 4,711,784 | 12/1987 | Yang | 426/5 |
| 4,720,384 | 1/1988 | DiLuccio et al. | 424/78 |
| 4,721,620 | 1/1988 | Cherukuri et al. | 426/6 |
| 4,722,845 | 2/1988 | Cherukuri et al. | 426/5 |
| 4,726,953 | 2/1988 | Carroll et al. | 426/5 |
| 4,740,376 | 4/1988 | Yang | 426/5 |
| 4,752,485 | 6/1988 | Sharma et al. | 426/99 |
| 4,766,036 | 8/1988 | Vaughn et al. | 428/364 |
| 4,771,118 | 10/1988 | Takamizawa et al. | 528/14 |
| 4,794,003 | 12/1988 | Cherukuri et al. | 426/6 |
| 4,816,265 | 3/1989 | Cherukuri et al. | 426/5 |
| 4,824,681 | 4/1989 | Schobel et al. | 426/5 |
| 4,828,857 | 5/1989 | Sharma et al. | 426/285 |
| 4,841,968 | 6/1989 | Dunn et al. | 128/335.5 |
| 4,870,035 | 9/1989 | Takamizawa et al. | 501/88 |
| 4,873,085 | 10/1989 | Fuisz | 424/400 |
| 4,885,175 | 12/1989 | Zibell | 426/5 |
| 4,892,736 | 1/1990 | Goodson | 424/435 |
| 4,911,934 | 3/1990 | Yang et al. | 426/5 |
| 4,915,958 | 4/1990 | Faust et al. | 426/3 |
| 4,929,447 | 5/1990 | Yang | 424/440 |
| 4,931,293 | 6/1990 | Cherukuri et al. | 426/5 |
| 4,933,190 | 6/1990 | Cherukuri et al. | 426/5 |
| 4,959,226 | 9/1990 | Chapdelaine et al. | 426/3 |
| 4,978,537 | 12/1990 | Song | 426/5 |
| 4,992,280 | 2/1991 | Chu et al. | 426/5 |
| 4,997,856 | 3/1991 | Fuisz | 514/777 |
| 5,000,965 | 3/1991 | Killeen et al. | 426/5 |
| 5,108,762 | 4/1992 | Broderick et al. | 426/5 |

FIG_2

FIG_3

Fig_6_

Fig_7_

FIG_8_

FIG_9_

Fig. 10

GRADUAL RELEASE STRUCTURES MADE FROM FIBER SPINNING TECHNIQUES

This application is a continuation of U.S. application Ser. No. 07/418,662, filed Oct. 10, 1989, now abandoned.

FIELD OF THE INVENTION

The invention is related to delivery systems for the gradual release of active agents and processes for making such systems and is particularly directed to delivery systems using heat sensitive active agents with biodegradable polymers and melt spinning processes for making such systems.

BACKGROUND OF THE INVENTION

The present invention is an advance in the art of delivery systems for the gradual release of active agents. This invention enables an active agent to be gradually released through the direct interaction of the agent and a solvent either within channels in the structure enclosing the active agent or through exposure of the active agent to the solvent when the structure enclosing the active agent is deformed or through diffusion of the active agent through the wall material.

Prior to the present invention, the gradual release of active agents, such as drugs, could be accomplished by the diffusion of the active agent through an encapsulating material. A discussion of such encapsulated structures is found in R. Dunn & D. Lewis, *Fibrous Polymers for the Delivery of Contraceptive Steroids to the Female Reproductive Tract*, Controlled Release of Pesticides and Pharmaceuticals 125–46 (D. Lewis ed. 1981), which describes fiber-like structures. Alternatively, an encapsulating shell around the active agent could be ruptured causing exposure of the active agent to various solvents.

Melt blending is another technique that was used prior to the present invention to obtain a mixture of active agent and support material to form a gradual release structure. In melt blending a polymer and an active agent are mixed and melted together. This molten mixture is then cast and solidified. The solidified mixture could then be ground or otherwise shaped for its intended end use. The present invention provides benefits over melt blending techniques by reducing the processing steps required with that technique and reducing the time that the active agent is exposed to heat during processing.

SUMMARY OF THE INVENTION

A delivery system is provided for the gradual release of an active agent. The system comprises an active agent and a wall material. The delivery system is formed by melt spinning a mixture of particles of active agent and wall material, having more than about 10 but less than about 55 percent by weight active agent, into a fiber. The fiber has a longitudinal dimension and a cross sectional dimension, the cross sectional dimension being at no greater than about 1 mm. The fiber has an exterior surface. The particles of active agent are dispersed through out the wall material such that the particles of active agent are gradually released from the fiber when the fiber is contacted with a solvent for the active agent.

A process is provided for making a delivery system for the gradual release of an active agent which comprises the steps of preparing a mixture of active agent and wall material, having more than about 10 but less than about 55 percent by weight active agent. This mixture is melt spun into a fiber using a die no greater in diameter than about 1 mm and at a temperature less than about 140° C. The melt spun fibers are then cut.

To aid in understanding the invention one is directed towards the drawings and the detailed description of the present preferred embodiment of the invention.

DETAILED DESCRIPTION OF PRESENTLY PREFERRED EMBODIMENT OF THE INVENTION

An embodiment of a structure made in accordance with the present invention is a fiber having a support matrix. The support matrix is made up of a wall material. An active agent is dispersed throughout the support matrix and may be in contact with itself forming a contiguous phase within the support matrix. The active agent, however, does not necessarily have to be in a contiguous phase. The ends of the support matrix have openings, exposing the active agent. Additionally, the active agent may be exposed along openings on the sides of the fiber. This structure may be made by stretching an already formed fiber. It is believed that the stretching action causes the wall material to orient itself longitudinally. The amount of active agent in this structure is from about 10 percent by weight to about 55 percent by weight. It is believed, however, that loading as low as a fraction of a percent of active agent will impart gradual release characteristics to the structure. The loading of the structure is influenced by the characteristics of the active agent such as its solubility or extractability from the support matrix.

After the fibers are formed by melt spinning they may be stretched by applying a draw, or stretching force, to the fibers. The draw can be applied at a winder or by venturi after the fibers exit the die. Other methods of stretching fibers known to the art may also be employed.

In this structure gradual release of the active agent occurs when the fiber is brought in contact with a solvent, or dispersing media, for the active agent. The wall material is less soluble in the solvent then the active agent and preferably the wall material should be substantially insoluble in the solvent under the conditions in which the fiber is being used.

It is presently believed that the solvent first dissolves the active agent in the openings at the ends of the support matrix. If the active agent is in a contiguous phase within the support matrix, the active agent in those openings is dissolved and spaces or channels in the support matrix are created. The solvent fills these channels and begins to dissolve the newly exposed active agent, which was in contact with the now dissolved active agent located in the openings at ends of the support matrix. Thus, the length of the channels in the support matrix gradually increases as the active agent directly in contact with the solvent is dissolved.

It is presently believed that the support matrix does not prevent the dissolution of the active agent because the active agent is in a contiguous phase. Rather, the support matrix serves to limit the rate of dissolution by restricting the area of active agent in direct contact with the solvent of the ends of the channels within the support matrix. Thus, the solvent can gradually work its way into the fiber by following the contiguous phase of active agent.

Additionally, it is presently believed that, depending on the stiffness of the wall material making up the support matrix, the support matrix can be deformed to expose new surface areas of active agent and thus bring them in direct contact with the solvent. For instance, when fibers are incorporated into a chewing material, the pressure from chewing will flatten, stretch, and deform the fibers exposing new surface areas of active agent to the solvent. This gradual release by deformation should occur even if the active agent is not in a contiguous phase. Higher molecular weight polymers used as wall material will not as readily exhibit this gradual release by deformation.

Furthermore, it is theorized that if the active agent is not in a contiguous phase the deformation of the support matrix may create channels, similar to those described above, through which the solvent can be brought in contact with the active agent.

Finally, depending on the wall material chosen, the active agent chosen, and the solvent being used, an extremely small amount of the active agent may dissolve by diffusion through the wall material.

Figure 1:
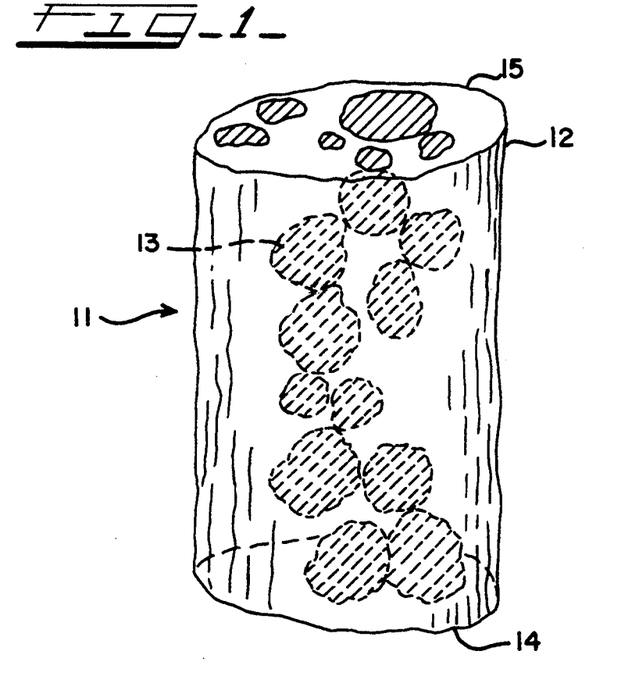
FIG. 1 is an illustration of a gradual release structure in fiber form.
Figure 2:
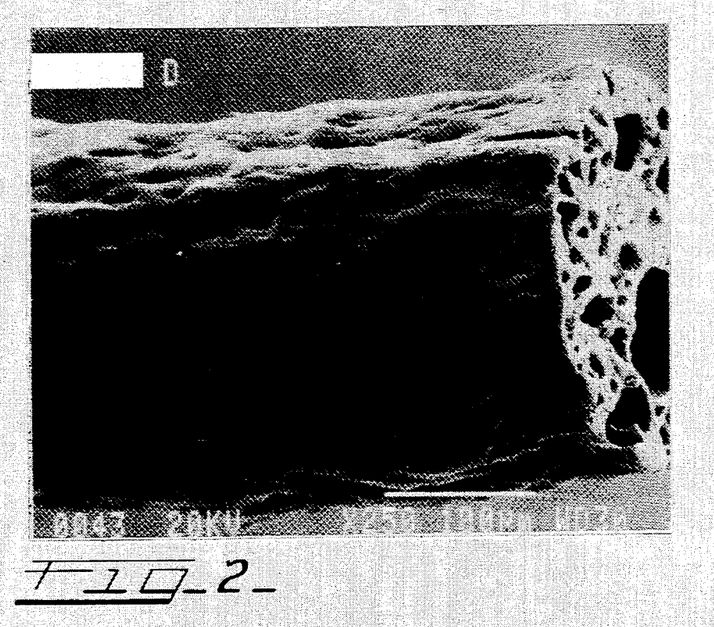
FIG. 2 is a Scanning Electron Photomicrograph (SEPM) of a gradual release structure showing the end and side of a fiber.
Figure 3:
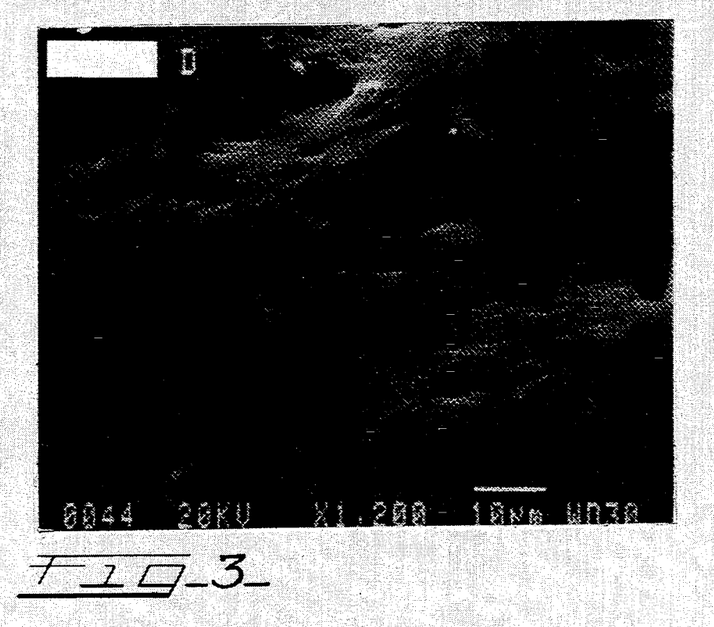
FIG. 3 is a SEPM of a gradual release structure showing the side of a fiber.

Another embodiment of a gradual release structure made in accordance with the present invention is illustrated in FIG. 1. In this embodiment the structure is in the form of a fiber 11 having a support matrix 12. The support matrix is made up of a wall material. An active agent 13 is dispersed throughout the support matrix and is in contact with itself forming a contiguous phase within the support matrix. The ends 14 and 15 of the support matrix have openings, exposing the active agent. Additionally, the active agent may be exposed along the sides of the fiber as can be seen in FIGS. 2 and 3. The active agent makes up at least about 25 percent of the structure by weight.

Figure 1A:
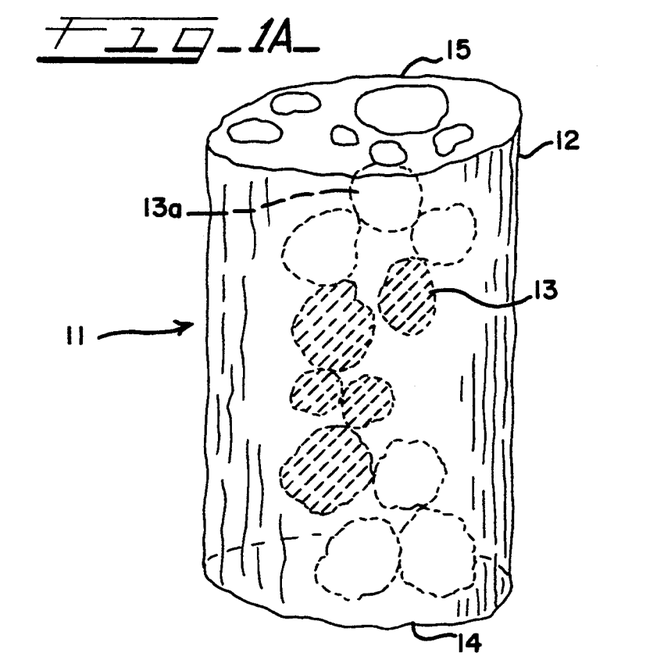
FIG. 1A is an illustration of the gradual release structure of FIG. 1 after it has been subjected to a solvent.

Gradual release of the active agent in this embodiment occurs when the fiber is brought in contact with a solvent, or dispersing media, for the active agent. The wall material is less soluble in the solvent then the active agent and preferably the wall material should be substantially insoluble in the solvent under the conditions in which the fiber is being used. As illustrated in FIG. 1A, the solvent first dissolves the active agent in the openings at the ends 14 and 15 of the support matrix. As this material is dissolved spaces or channels 13a in the support matrix are opened. The solvent fills these channels and begins to dissolve the newly exposed active agent, which was in contact with the now dissolved active agent located in the openings at ends of the support matrix. Thus, the length of the channels in the support matrix gradually increase as the active agent directly in contact with the solvent is dissolved.

It is presently believed that the support matrix does not prevent the dissolution of the active agent because the active agent is in a contiguous phase. FIG. 1 and 1A. Rather, the support matrix serves to limit the rate of dissolution by restricting the area of active agent in direct contact with the solvent to the end of the channels within the support matrix. Thus, the solvent can gradually work its way into the fiber by following the contiguous phase of active agent. Additionally, depending on the wall material chosen, the active agent chosen, and the solvent being used a small amount of the active agent may dissolve by diffusion through the wall material. Gradual release by deformation may also be exhibited by this structure.

Figure 4:
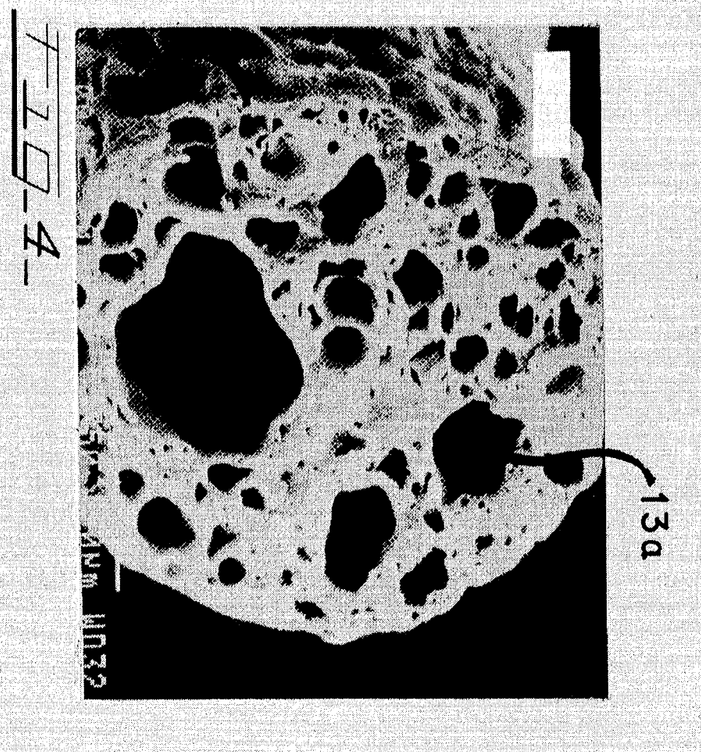
FIGS. 4 & 5 are SEPMs of a gradual release structure showing the ends of a fiber and the channels within the encapsulating structure.
Figure 5:
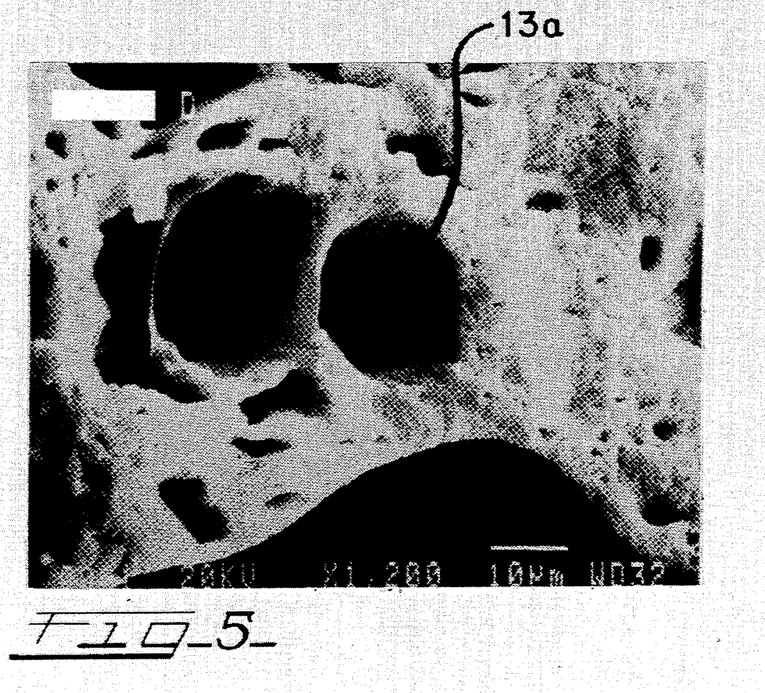
Figure 6:
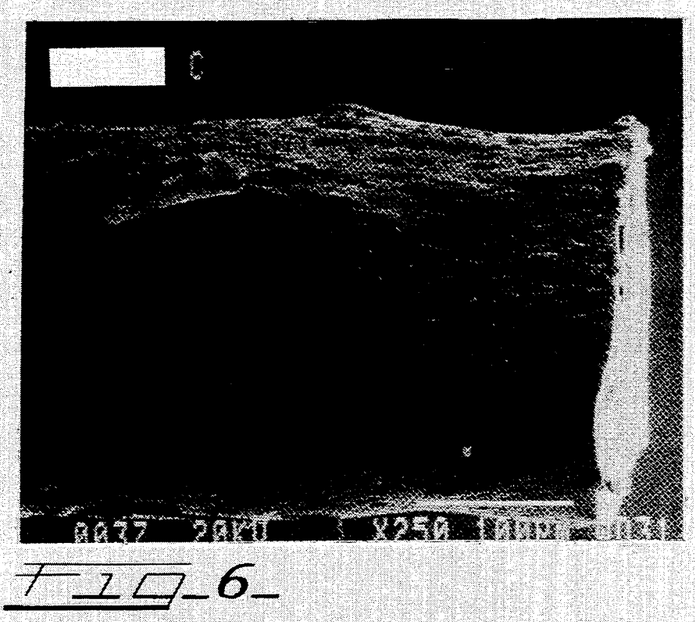
FIG. 6 is an SEPM showing the side and end of a fiber.
Figure 7:
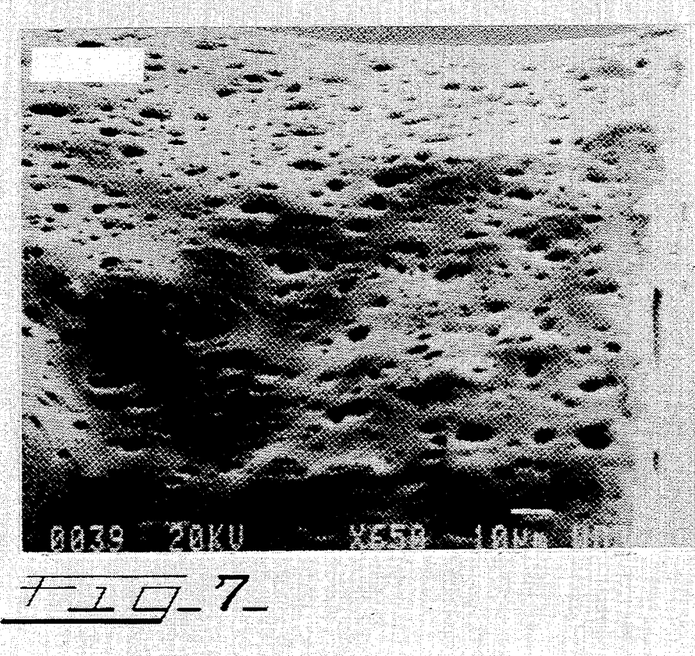
FIG. 7 is a SEPM showing the side of a fiber.

FIGS. 4 and 5 contain SEPMs of fibers made in accordance with the present invention. These fibers were subjected to a solvent. The spaces or channels 13a where the active agent was dissolved out are shown in these SEPMs.

Figure 10:
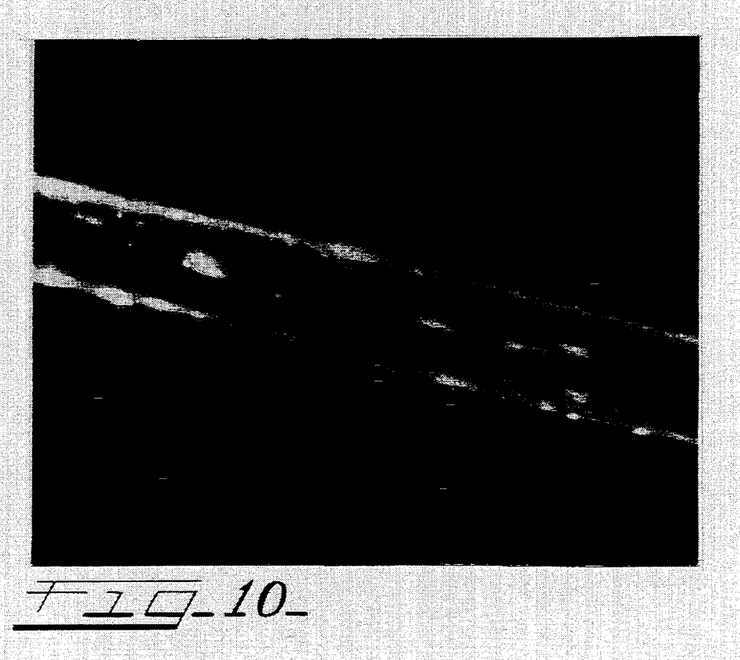
FIG. 10 is a SEPM of a gradual release structure showing a fiber with a crystalline active agent oriented along the length of the fiber parallel to the longitudinal axis.

Another embodiment of a gradual release structure made in accordance with the present invention is illustrated in FIG. 10. In this embodiment the active agent is crystaline in form. Here it is aspartame. In this embodiment the crystaline active agent is oriented along the length of the fiber or parallel to the longitudinal direction of the fiber.

The active agent can be any material such as artificial sweeteners, powdered flavor oil, or drugs, which the gradual release of may be desired. They must be solid or in the form of powders, including liquids encapsulated by spray drying techniques or liquids adsorbed or absorbed into or onto a supporting matrix, i.e., silica, zeolite, carbon black, or porous matrices. Combinations of different active agents in the same structure may also be employed. For purposes of illustration, possible active agents may be: high intensity sweeteners, such as aspartame, alitame, acesulfam-k and its salts, saccharin and its salts, thaumatin, sucralose, cyclamic acid and its salts, monellin, and dihydrochalcones; acidulents, such as malic acid, citric acid, tartaric acid, and fumaric acid; salt, such as sodium chloride and potassium chloride; bases, such as, magnesium hydroxide and urea; flavors, such as spray dried natural or synthetic flavors, flavor adsorbed onto silica, and absorbed into maltodextrin; flavor modifiers, such as thaumatin; breath fresheners, such as zinc chloride, encapsulated menthol, encapsulated anise, zinc glucinate, and encapsulated chlorophyll; pesticides and herbicides such as Abate ®, Malathion ® (active ingredient, Diethyl 2-(dimethexyphosphionthioylthio) succinate), Dursban ®, Naned ®, Fenthion ®, and sodium salt of (2,4-Dichlorophienoxy) acetic acid; pharmaceuticals such as ibuprofen, antacids, anti-inflammatory substances, coronary dilators, cerebral dilators, peripheral vasodilators, anti-infectives, psychotropics, anti-manics, stimulants, anti-histamines, laxatives, decongestants, vitamins, gastro-intestinal sedatives, anti-diarrheal preparations, anti-anginal drugs, vasodilators, anti-arrhythmics, anti-hypertensive drugs, anti-coagulants, analgesics, sedatives, neuromuscular drugs, mineral and nutritional additives, anabolic drugs, expectorants, and cough suppressants; and fertilizers.

Care must be taken to avoid the degradation of the active agent from high temperatures, shear, or other conditions, which may occur during formation. The wall material can be any spinnable synthetic or natural polymer such as polyethylene, polyvinylacetate, polyesters, chitosan, and copolymers and polymer blends of these polymers. The active agent and wall material must meet the solubility requirements discussed above. Additionally, they must be immiscible with each other and capable of being uniformly dispersed when mixed together during the melt spinning procedure.

While any extrudable thermoplastic is suitable, the use of biodegradable polymers is beneficial for many applications. Examples of biodegradable polymers useful in this invention include copolymers of lactic and glycolic acid (PLGA), polypropylene fumarate (PPF), copolymers of fumaric and succinic acids, polyalkyl-L-glutamic acid, polyglycolic acid, poly-methyl-L-glutamic acid, polymers of glutamic acid, copolymers of glutamic acid, poly—1—glutamic acid and lysine.

The release rate of the resulting structure can be modified by crosslinking the polymer. For example, crosslinking of the polylactic/polyglycolic acid copolymer can be achieved by maleic anhydride.

The gradual release structures of the present invention may have an application in any situation in which the gradual release of an active agent is needed.

Gradual release structures that embody the present invention are made by melt spinning a uniform mixture of active agent and wall material into a fiber. The general principles for melt spinning polymers are well known in the art and are described in F. Billmeyer, Jr., *Text Book of Polymer Science;* 518–22 (Wiley International Edition, 2nd), which is incorporated herein by reference. In this process a mixture of a polymer for the wall material and an active agent are prepared in powder or pellet form. The particles of polymer and active agent are mixed together into a homogeneous phase. The concentration of active agent in this mixture is such that the particles of active agent may be in contact with each other. The mixture is melt spun to produce fibers. These fibers are then gently broken into smaller sizes. Any grinding machine or knife which reduces the length of fiber without excessively damaging the support matrix is suitable. Fiber brittleness eases the cutting process of the fiber and can be achieved by concentrating the solid active agent particles.

The fact that a polymer or polymer blend initially shows an unacceptably high pressure for extrusion, does not automatically eliminate the possibility of using it in this process. Processability often can be improved by increasing the processing temperature, introducing plasticizers, changing nozzle dimensions, adding dispersing agents, or modifying it by blending with other polymers.

By way of example, this process is carried out on two types of equipment.

Model 1125 Instron Capillary Rheometer

A Model 1125 Instron Capillary Rheometer, with capillary hole diameter of 152 microns is used to extrude fibers. The barrel diameter is ⅜ inches. The die has a Length to diameter ratio of 0.083 and has 1 hole. In this application of the process L-aspartyl-L-phenylalanine methyl ester (Aspartame) is used as the active agent. A polyvinylacetate (PVAc) having a molecular weight from about 50,000 to 80,000 is chosen as the wall material.

This laboratory scale Capillary Rheometer can not provide enough mixing action during extrusion. Thus, prior to extrusion, samples are pre-blended by two methods. In one method, PVAc is dissolved in Methylene Chloride ($CH_2Cl_2$) at room temperature, and then Aspartame is mixed into this solution. The solvent is evaporated overnight under vacuum at 60° C. to form a solid material. This material is ground to a powder to facilitate addition into the rheometer.

This method is indicated in Table 1 as "Solution Blended." In the other method, samples are prepared for extrusion by directly blending the Aspartame with a polymer melt of the wall material in a heated beaker at 140° C. The blend is dried under vacuum at 60° C. for about 5 hours to remove water. This method is indicated in Table 1 as "Melt Blended."

Using these two methods of mixing the wall material and the active agent, fibers with varying amounts of Aspartame are produced. The parameters used for these examples are set out in the following Table 1. The Jet Speed is the speed of the material being meltspun in the capillary.

TABLE 1

|  | Temp. | Jet Speed (m/min) | Extrusion Load (kgf) |
|---|---|---|---|
| Example 1) | | | |
| Aspartame | 140½ C. | 5 | 13 |
| 17 wt. % | | 10 | 18 |
| in PVAc | | 20 | 32 |
| (Solution Blended) | | 50 | 57 |
| | | 100 | 76 |
| Example 2) | | | |
| Aspartame | 150° C. | 5 | 18 |
| 17 wt. % | | 10 | 23 |
| in PVAc | | 20 | 34 |
| (Solution Blended) | | 50 | 51 |
| | | 100 | 68 |
| Example 3) | | | |
| Aspartame | 140° C. | 5 | 41–59 |
| 17 wt. % | | 10 | 23–68 |
| in PVAc | | 20 | 45–113 |
| (Melt Blended) | | 50 | 68 |
| Example 4) | | | |
| Aspartame | 140° C. | 5 | 13 |
| 29 wt. % | | 10 | 16 |
| in PVAc | | 20 | 20 |
| (Solution Blended) | | 100 | 52 |
| Example 5) | | | |
| Aspartame | 150° C. | 5 | 9 |
| 29 wt. % | | 10 | 13 |
| in PVAc | | 20 | 17 |
| (Solution Blended) | | 50 | 25 |
| | | 100 | 36 |
| | | 200 | 50 |
| | | 500 | 59 |
| Example 6) | | | |
| Aspartame | 140° C. | 5 | 32 |
| 29 wt. % | | 10 | 45 |
| in PVAc | | 20 | 90–180 |
| (Melt Blended) | | 50 | less than 180 |
| Example 7) | | | |
| Aspartame | 140° C. | 5 | 14 |
| 35 wt. % | | 10 | 17 |
| in PVAc | | 20 | 25 |
| (Solution Blended) | | 50 | 36 |
| Example 8) | | | |
| Aspartame | 140° C. | 5 | 10 |
| 35 wt. % | | 10 | 12 |
| in PVAc | | 20 | 18 |
| (Solution Blended) | | 50 | 27 |
| | | 100 | 41 |
| | | 200 | 55 |
| Example 9) | | | |
| Aspartame | 140° C. | 5 | 36–41 |
| 35 wt. % | | 10 | 54–64 |
| in PVAc | | 20 | 113–136 |

TABLE 1-continued

|  | Temp. | Jet Speed (m/min) | Extrusion Load (kgf) |
|---|---|---|---|
| (Melt Blended) |  | 50 | 272–363 |

Table 1, shows that the spinnability of PVAc blends is good and not highly dependent on the Aspartame loading level. The extrudates of PVAc/Aspartame blends shown in Table 1 are brittle at 17% Aspartame loading. Brittleness increases as the Aspartame loading level increases. The diameter of the extruded fibers due to die swell is slightly larger than the capillary, which is 152 microns.

The extruded fibers are gently ground with a mortar and pestle. The diameter to length ratio of these ground fibers is narrowly distributed with no major breakage of fibers along the longitudinal direction.

Figure 8:
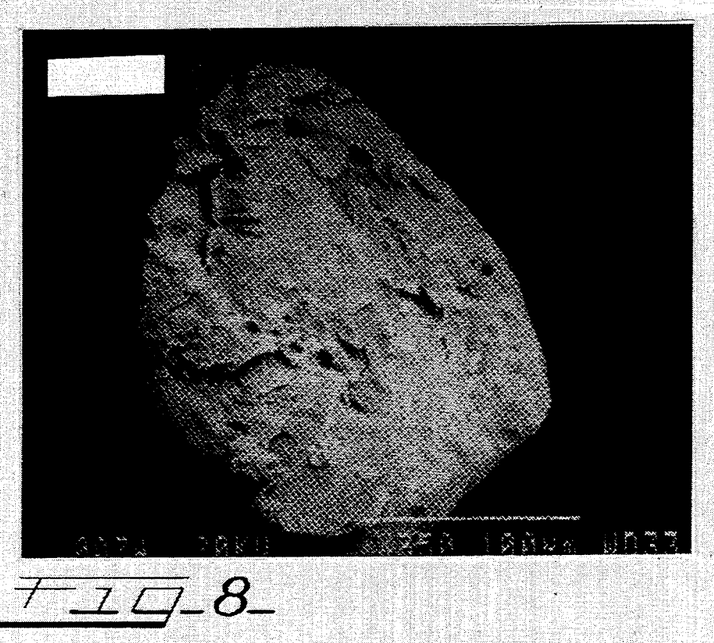
FIGS. 8 & 9 are SEPMs showing the ends of a fiber.
Figure 9:
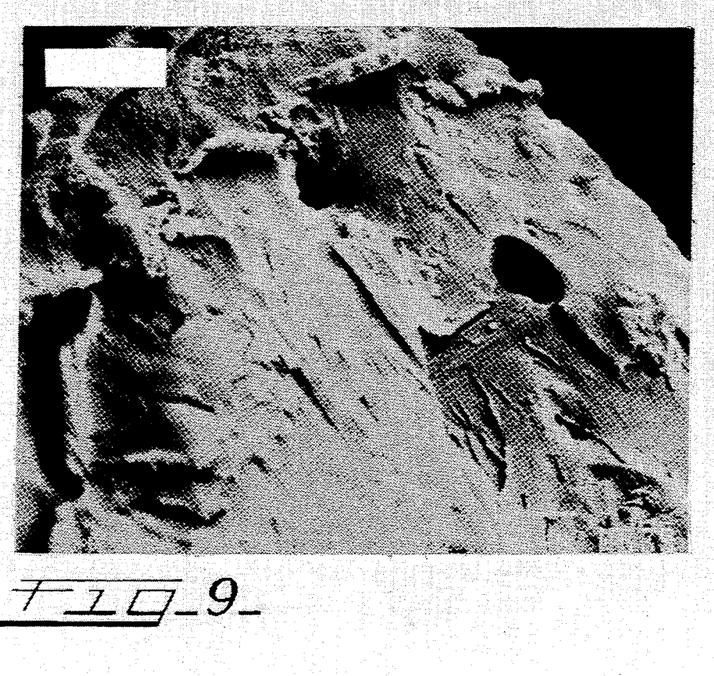

FIGS. 2 through 5 are SEPMs of fibers having 29% by weight Aspartame in PVAc that are prepared by the solution blending technique described above and extruded at 150° C. FIGS. 6 through 9 are SEPMs of fibers having 17% by weight Aspartame in PVAc that are prepared by the melt blending technique described above and extruded at 140° C. Both samples are extracted with water as the solvent for four hours. The spaces shown in the SEPMs are places from which Aspartame is dissolved. FIGS. 8 and 9 show that at 17% loading, the solid particles of Aspartame are isolated in the polymer. Thus, Aspartame could not completely dissolve out into the water without physical deformation of the polymeric structure. At 29% loading, FIGS. 4 and 5, however, the solid particles of Aspartame form a contiguous phase as illustrated in FIG. 1. Thus, channels in the encapsulating structure are opened and the Aspartame is gradually released, until virtually none remains.

Liquid Chromatography analysis is carried out on the fibers spun at 140° C. and at 150° C. in examples 1 through 9 to determine the amount of thermal degradation of Aspartame occurring during the melt spinning process discussed above. At 140° C. thermal degradation of Aspartame is less than 10%. At 150° C. the percent thermal degradation of Aspartame approached 20%.

The residence time of Aspartame/polymer blend in the Capillary Rheometer used to prepare the above samples is about twenty minutes. In production scale spinning, residence time could be reduced to around 20 seconds to two minutes. This would greatly reduce the degree of Aspartame degradation. At 90°–100° C. using a twin screw extruder at 2 minutes residence time, no degradation is observed.

TWIN SCREW EXTRUDER

In Examples 10–28 a type LSM 30:34 twin screw extruder from American Leistritz Extruder Corporation is used to produce the fibers. Generally, a homogeneous mixture of wall material and active agent in powdered form are poured into a hopper on the extruder. The hopper feed screws force the mixture through heated sections of the extruder, melting the polymer, and then through a die. The die consists of a plurality of holes having a specific diameter and length. Upon leaving the die the fibers are stretched by either drawing them with a winder or by blowing air past them with a venturi.

The twin screw extruder consists in this case of two sets of eight element screws. These screws can operate in an intermeshing fashion in either a co-rotational or a counter rotational mode, These screws can function as kneading elements or conveying elements. For the following examples four kneading elements alternating with four conveying elements are used. Other configurations are possible and will depend on the process conditions and the types of materials being melt spun and the degree of mixing required.

The twin screw extruder used in the following examples is divided into eight zones. The temperature of each zone is controlled. For example, a mixture of percent by weight PVAc with a molecular weight of about 30,000, 25 percent by weight PVAc with a molecular weight of about 15,000, and 25 percent by weight Aspartame is melt spun to produce fibers. Operating the extruder with a 1 mm die having 5 holes at 30 rpm, results in the production of 5 pounds of fiber per hour. The following temperatures in degrees centigrade are used for each zone:

| Zone | Temp. |
|---|---|
| Feeding or hopper zone | 85 |
| 2 | 95 |
| 3 | 95 |
| 4 | 95 |
| 5 | 95 |
| 6 | 95 |
| 7 | 95 |
| Die or last zone | 102 |

Operating the extruder with a 1 mm die having holes at 333 rpm, results in the production of 50 pounds of fiber per hour. The following temperatures in degrees centigrade are used for each zone:

| Zone | Temp. |
|---|---|
| Feeding or hopper zone | 85 |
| 2 | 97 |
| 3 | 97 |
| 4 | 97 |
| 5 | 97 |
| 6 | 97 |
| 7 | 97 |
| Die or last zone | 102 |

In the following examples dies having a diameter of 1 mm and 0.3 mm are used. The 1 mm die has holes and has a diameter to length ratio of about 4. The 0.3 mm die has 34 holes and has a diameter to length ratio of 2.3. The temperatures set out in these examples are an average of all heating zones on the extruder.

EXAMPLE 10

Using a 1 mm die, fibers having 10% by weight Acesulfam-K (a high intensity sweetener purchased from Hoecht, of W. Germany) as the active agent and having PVAc with a molecular weight of about 50,000–80,000 as the wall material are extruded at 110°–115+ C. The fibers are drawn by a winder and have a thickness of 0.2–0.3 mm. The Acesulfam-K particles disperse very well in the fibers and the fibers exhibit a gradual release of the active agent when chewed alone.

EXAMPLE 11

Using a 1 mm die, fibers having by weight Acesulfam-K as the active agent and having PVAc with a molecular weight of about 50,000–80,000 as the wall material are extended at 110° C. The fibers are drawn by a winder. The fibers are between 0.3–0.4 mm in thickness. The Acesulfam-K particles disperse very well in the fibers and the fibers exhibit a gradual release of the active agent when chewed alone.

EXAMPLE 12

Using a 1 mm die, fibers having 10% by weight Aspartame as the active agent and having PVAc with a molecular weight of about 50,000–80,000 as the wall material are extruded at 100° C. The fibers are drawn by a winder and have a thickness of 0.2–0.3 mm. The Aspartame disperses very well in the fibers and the fibers exhibit a gradual release of the active agent when chewed alone.

EXAMPLE 13

Using a 1 mm die, fibers having 10% by weight Aspartame as the active agent and having PVAc with a molecular weight of about 50,000–80,000 as the wall material are extruded at 100° C. The fibers are drawn by the winder and have a thickness of about 0.2 mm. The Aspartame disperses very well in the fibers and the fibers exhibit an excellent gradual release of the active agent when chewed alone.

EXAMPLE 14

Using a 1 mm die, fibers having 35% by weight Sodium Saccharin as the active agent and having PVAc with a molecular weight of about 50,000–80,000 as the wall material are extruded at 100° C. The fibers are drawn at the winder and are 0.4–0.5 mm thick. The Sodium Saccharin dispersed very well in the fibers, although the fibers are softer than those of examples 10–13. The fibers exhibit a gradual release of the active agent when chewed alone.

EXAMPLE 15

Using a 1 mm die, fibers having 35% by weight Saccharin Acid as the active agent and having PVAc with a molecular weight of about 50,000–80,000 as the wall material are extruded at 100° C. The fibers are drawn at the winder and are 0.4–0.5 mm thick. The Saccharin Acid disperses very well in the fiber, although the fibers are softer than those of examples 10–13. The fibers exhibit a gradual release of the active agent when chewed alone.

EXAMPLE 16

Using a 1 mm die, fibers having 6.13% by weight NaCl, 3.87% by weight KCl as the active agents and having PVAc with a molecular weight of about 30,000 as the wall material are extruded at 113° C. The fibers are drawn at the winder and are 0.12 mm in thickness. The NaCl and KCl particles are dispersed in the fiber. The fibers exhibit good gradual release of the active agent when chewed alone.

EXAMPLE 17

Using a 1 mm die, fibers having 6.13% by weight NaCl, 3.87% by weight KCl as the active agents and having PVAc with a molecular weight of about 15,000 as the wall material are extruded at 90° C. The fibers are drawn by air blowing and are 0.12 mm in thickness and are slightly weaker than the fibers of Example 16. The fibers exhibit a gradual release of the active agent when chewed alone.

EXAMPLE 18

Using a 1 mm die fibers having 24.52% by weight NaCl, and 15.48% KCl by weight as the active agents and having Allied Chemical PE 735 as the wall material are extruded at 85°–90° C. The fibers are 0.96 mm thick and are drawn by air blowing. The fibers exhibit gradual release of salts.

EXAMPLE 19

Using a 1 mm die, fibers having 25% by weight Diamonium Phosphate as the active agent and having PVAc with a molecular weight of about 50,000–80,000 as the wall material are extruded at 100° C. The fibers are drawn by air blowing and have a thickness of 0.20–0.38 mm.

EXAMPLE 20

Using a 1 mm die, fibers having 25% by weight NaF as the active agent and having PVAc with a molecular weight of 50,000–80,000 are extruded at 90°–100° C. The fibers are drawn by air blowing and have a thickness of 0.18–0.25 mm.

EXAMPLE 21

Using a 1 mm die, fibers having 25% by weight $Mg(OH)_2$ as the active agent and having PVAc with a molecular weight of about 50,000–80,000 as the wall material are extruded at 90°–100° C. The fibers are drawn by air blowing and have a thickness of 0.25 mm.

EXAMPLE 22

Using a 1 mm die, fibers having 25% by weight Acesulfam-K as the active agent and having PVAc with a molecular weight of about 30,000 as the wall material are extruded at 90°–100° C. The fibers are drawn by air blowing and have a thickness of 0.13 mm.

EXAMPLE 23

Using a 0.3 mm die, fibers having 25% by weight Aspartame as the active agent and having PVAc with a molecular weight of about 50,000–80,000 as the wall material are extruded at 90°–100°½ C. In making the fibers of this example prior to extrusion the PVAc and Aspartame are premixed in methylene chloride, following the solution blended method described above. The fibers are drawn by a winder and have a thickness of 0.127 mm.

EXAMPLE 24

Using a 1 mm die, fibers having 10% by weight ibuprofen as the active agent and having 90% by weight poly-1-glutamic acid as the wall material are extruded at 100° C. The fibers are drawn to a diameter of 0.2–0.3 mm by a winder.

EXAMPLE 25

Using a 1 mm die, fibers having 25% by weight thiamine as the active agent and having 75% by weight poly-methyl-L-glutamic acid as the wall material are extruded at 100° C. The fibers are drawn to a diameter of 0.2–0.3 mm by a winder.

EXAMPLE 26

Using a 0.3 mm die, fibers having 25% by weight ascorbic acid as the active agent and having 75% by weight polypropylene fumarate as the wall material are extruded at 90° C. The fibers are drawn to a diameter of 0.15 mm by a winder.

EXAMPLE 27

Using a 1.0 mm die, fibers having 10% by weight of 25% spray dried malathion as the active agent and having 75% by weight polyglycolic acid as the wall material are extruded at 140° C. No draw is applied.

EXAMPLE 28

Using a 1.0 mm die, fibers having 50% by weight of a sodium salt 2, 4-D as the active agent and having 50% by weight polylactic acid as the wall material are extruded at 130° C. No draw is applied.

Many variations of the invention suggest themselves to those skilled in the art in view of the above disclosure without departing from the spirit and scope of this invention.

I claim:

1. A delivery system for the gradual release of an active agent, the delivery system comprising an active agent and a wall material, wherein the delivery system is formed by meltspinning into a fiber a mixture of active agent and wall material, the mixture having more than zero but less than about 55 percent by weight active agent, the resulting fiber having a longitudinal dimension and a cross sectional dimension, wherein the cross sectional dimension is no greater than about 1 mm, the fiber further having an exterior surface wherein the wall material comprises a majority of the exterior surface and the active agent comprises a minority of the exterior surface with particles of active agent dispersed throughout the wall material and substantially contiguously throughout the fiber, the fiber further having openings on either end thereby exposing the active agent to a solvent specific to the active agent.

2. A delivery system for the gradual release of an active agent, the delivery system comprising an active agent and a wall material, wherein the delivery system is formed by meltspinning into a fiber a mixture of active agent and wall material, the mixture having more than about 10 but less than about 55 percent by weight active agent, the resulting fiber having a longitudinal dimension and a cross sectional dimension, wherein the cross sectional dimension is no greater than about 1 mm, the fiber further having an exterior surface, the particles of active agent dispersed throughout the fiber and the exterior surface such that the particles of active agent are gradually released from the fiber when the fiber is contacted with a solvent specific to the active agent.

3. The delivery system of claim 2 wherein the active agent comprises flavor.

4. The delivery system of claim 2 wherein the active agent comprises sweetener.

5. The delivery system of claim 2 wherein the active agent comprises fertilizer.

6. The delivery system of claim 2 wherein the active agent comprises pesticide.

7. The delivery system of claim 2 wherein the active agent comprises a pharmaceutical.

8. The delivery system of claim 2 wherein the active agent comprises acesulfam K.

9. The delivery system of claim 2 wherein the active agent comprises aspartame.

10. The delivery system of claim 2 wherein the wall material comprises poly-1-glutamic acid and the active agent comprises ibuprofen.

11. The delivery system of claim 2 wherein the wall material comprises poly-methyl-L-glutamic acid and the active agent comprises thiamine.

12. The delivery system of claim 2 wherein the wall material comprises polypropylene fumarate and the active agent comprises ascorbic acid.

13. The delivery system of claim 2 wherein the wall material comprises polyglycolic acid and the active agent comprises Diethyl 2-(dimethoxyphosphinothioythio) succinate.

14. The delivery system of claim 2 wherein the wall material comprises polylactic acid and the active agent comprises a sodium salt of (2,4-Dichlorophenoxy) acetic acid.

15. A delivery system for the gradual release of an active agent, the delivery system comprising an active agent and a wall material, wherein the delivery system is formed by meltspinning into a fiber a mixture of active agent and wall material, the mixture having more than about 25 but less than about 55 percent by weight active agent, the resulting fiber having a longitudinal dimension and a cross sectional dimension, the cross sectional dimension being no greater than about 1 mm, the fiber further having particles of active agent dispersed throughout the wall material; the fiber further having openings on either end thereby exposing the active agent to a solvent specific to the active agent.

16. The delivery system of claim 15 wherein the wall material comprises poly-methyl-L-glutamic acid and the active agent comprises thiamine.

17. The delivery system of claim 15 wherein the wall material comprises polypropylene fumarate and the active agent comprises ascorbic acid.

18. The delivery system of claim 15 wherein the wall material comprises polyglycolic acid and the active agent comprises Diethyl 2-(dimethoxyphosphinothioythio) succinate.

19. The delivery system of claim 15 wherein the wall material comprises polylactic acid and the active agent comprises a sodium salt of (2,4-Dichlorophenoxy) acetic acid.

20. A delivery system for the gradual release of an active agent, the delivery system comprising a crystalline active agent and a wall material wherein the delivery system is formed by melt spinning into a fiber a mixture of active agent and wall material, the mixture having more than 10 but less than about 55 percent by weight active agent, the resulting fiber having a longitudinal dimension and a cross sectional dimension, the cross sectional dimension being no greater than about 1 mm, wherein the crystalline active agent is oriented parallel to the longitudinal dimension of the fiber, and dispersed throughout the fiber whereby the particles of active agent are gradually released from the fiber when the fiber is contacted with a solvent specific to the active agent.

21. The delivery system of claim 20 wherein the active agent is aspartame.

22. The drug delivery system of claim 1 in which the mixture of active agent and wall material is free from solvent for the wall material.

23. The drug delivery system of claim 2 in which the mixture of active agent and wall material is free from solvent for the wall material.

24. The drug delivery system of claim 15 in which the mixture of active agent and wall material is free from solvent for the wall material.

25. The drug delivery system of claim 20 in which the mixture of active agent and wall material is free from solvent for the wall material.

26. A delivery system for the gradual release of an active agent comprising:
   a) a mixture of an active agent and a wall material in a fiber having a longitudinal surface;
   b) the mixture having less than about 55 percent by weight active agent;
   c) the wall material forming a support matrix within the fiber;
   d) the support matrix having a plurality of interconnected channels with openings in the longitudinal surface of the fiber;
   e) the active agent in the channels and in the longitudinal surface of the fiber;
   f) whereby the active agent is gradually released from the fiber when the fiber is contacted with a solvent specific to the active agent, 27. A delivery system for the gradual release of an active agent comprising:
   a) a support matrix in a fiber having a longitudinal and two end surfaces;
   b) the support matrix having a plurality of interconnected channels with openings on the longitudinal and end surfaces of the fiber;
   c) an active agent in the channels and in the longitudinal and end surfaces of the fiber;
   d) the fiber having more than about 10 and less than about 55 percent by weight active agent;
   e) whereby the active agent is gradually released from the fiber when the fiber is contacted with a solvent specific to the active agent.

28. A delivery system for the gradual release of an active agent comprising:
   a) an active agent and a wall material, wherein the delivery system is formed by melt spinning a mixture of active agent and wall material into a fiber;
   b) the mixture having less than about 55 percent by weight active agent;
   c) the resulting fiber having:
      i) a longitudinal and two end surfaces;
      ii) a support matrix comprising the wall material;
      iii) the active agent dispersed substantially contiguously throughout the support matrix and being present in the longitudinal and end surfaces of the fiber;
   d) whereby the active agent is gradually released from the fiber when the fiber is contacted with a solvent specific to the active agent.

29. A delivery system for the gradual release of an active agent comprising:
   a) an active agent and polyvinyl acetate, wherein the delivery system is formed by melt spinning a mixture of active agent and polyvinyl acetate into a fiber;
   b) the mixture having less than about 55 percent by weight active agent;
   c) the resulting fiber having:
      i) a longitudinal and two end surfaces;
      ii) a support matrix comprising the polyvinyl acetate;
      iii) the active agent dispersed substantially contiguously throughout the support matrix and being present in the exterior longitudinal and end surfaces of the fiber;
   d) whereby the active agent is gradually released from the fiber when the fiber is contacted with a solvent specific to the active agent.

* * * * *